(12) United States Patent
Siryk et al.

(10) Patent No.: US 8,431,391 B2
(45) Date of Patent: Apr. 30, 2013

(54) PLANT FOR PRODUCING AN OXYGEN-CONTAINING ADDITIVE AS AN ECOLOGICALLY BENEFICIAL COMPONENT FOR LIQUID MOTOR FUELS

(75) Inventors: Yury Paul Siryk, Pavlograd (UA); Ivan Peter Balytski, Pavlograd (UA); Volodymyr George Korolyov, Pavlograd (UA); Olexiy Nick Klishyn, Pavlograd (UA); Vitaly Nick Lnianiy, Pavlograd (UA); Yury Alex Lyakh, Pavlograd (UA); Victor Valery Rogulin, Pavlograd (UA)

(73) Assignee: U.S. Department of Energy, Washington, DC (US)

( * ) Notice: Subject to any disclaimer, the term of this patent is extended or adjusted under 35 U.S.C. 154(b) by 308 days.

(21) Appl. No.: 12/606,151

(22) Filed: Oct. 26, 2009

(65) Prior Publication Data
US 2010/0136674 A1    Jun. 3, 2010

Related U.S. Application Data

(63) Continuation of application No. PCT/IB2007/004121, filed on Dec. 27, 2007.

(30) Foreign Application Priority Data

Apr. 26, 2007  (UA) .................................. 200704667

(51) Int. Cl.
*C12M 1/00*    (2006.01)
*C12M 3/00*    (2006.01)
*C02F 3/34*    (2006.01)

(52) U.S. Cl.
USPC ....... 435/289.1; 435/300.1; 435/41; 435/132; 435/262.5; 435/266; 435/264; 435/298.1

(58) Field of Classification Search .............. 435/289.1, 435/300.1, 41, 132, 298.1, 262.5, 266, 264
See application file for complete search history.

(56) References Cited

U.S. PATENT DOCUMENTS

| | | | | |
|---|---|---|---|---|
| 6,335,191 B1 * | 1/2002 | Kiplinger et al. | .......... | 435/252.1 |
| 2007/0141691 A1 * | 6/2007 | Hirl | .............................. | 435/161 |

(Continued)

FOREIGN PATENT DOCUMENTS

| | | | |
|---|---|---|---|
| CZ | 300046 B6 * | 1/2009 | |
| EP | 1790732 A1 * | 5/2007 | |

OTHER PUBLICATIONS

Dictionary.com, "Cavity," available at http://dictionary.reference.com/browse/cavity?s=t (last visited Jun. 7, 2012).

(Continued)

*Primary Examiner* — Nathan Bowers
(74) *Attorney, Agent, or Firm* — Michelle P. Nguyen; Michael J. Badagliacca; John T. Lucas

(57) ABSTRACT

A plant for producing an oxygen-containing additive for liquid motor fuels comprises an anaerobic fermentation vessel, a gasholder, a system for removal of sulphuretted hydrogen, and a hotwell. The plant further comprises an aerobic fermentation vessel, a device for liquid substance pumping, a device for liquid aeration with an oxygen-containing gas, a removal system of solid mass residue after fermentation, a gas distribution device; a device for heavy gases utilization; a device for ammonia adsorption by water; a liquid-gas mixer; a cavity mixer, a system that serves superficial active and dispersant matters and a cooler; all of these being connected to each other by pipelines. The technical result being the implementation of a process for producing an oxygen containing additive, which after being added to liquid motor fuels, provides an ecologically beneficial component for motor fuels by ensuring the stability of composition fuel properties during long-term storage.

11 Claims, 1 Drawing Sheet

U.S. PATENT DOCUMENTS

2009/0176289 A1* 7/2009 Friedmann .................... 435/167
2009/0200231 A1* 8/2009 Walton et al. ................. 210/631
2011/0165638 A1* 7/2011 Kotelko et al. ............... 435/134

OTHER PUBLICATIONS

Merriam-Webster Dictionary, "Dispersant," available at http://www.merriam-webster.com/dictionary/dispersant (last visited Jun. 7, 2012).

Dictionary.com, "distiller," available at http://dictionary.reference.com/browse/distiller?s=t (last visited Jun. 7, 2012).

Dictionary.com, "Gasholder," available at http://dictionary.reference.com/browse/gasholder?s=t (last visited Jun. 7, 2012).

Merriam-Webster Dictionary, "Hot Well," available at http//www.merriam-webster.com/dictionary/hot%20well (last visited Jun. 7, 2012).

Dictionary.com, "Hot well," available at http://dictionary.reference.com/browse/hot+well?s=t (last visited Jun. 7, 2012).

Dictionary.com, "Mixer," available at http://dictionary.reference.com/browse/mixer?s=t (last visited Jun. 7, 2012).

Merriam-Webster Dictionary, "Superficial," available at http/;/www.merriam-webster.com/dictionary/superficial (last visited Jun. 7, 2012).

Merriam-Webster Dictionary, "Surface-active," available at http://www.merriam-webster.com/dictionary/surface-active (last visited Jun. 7, 2012).

* cited by examiner

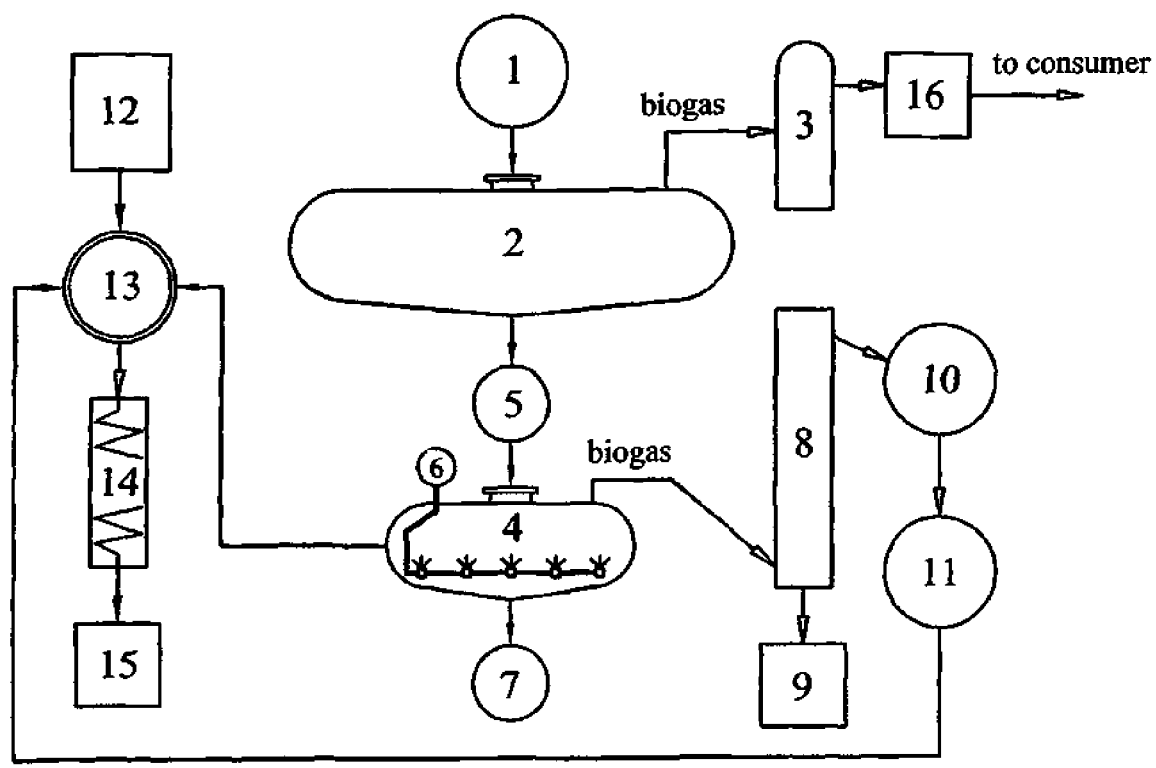

US 8,431,391 B2

PLANT FOR PRODUCING AN OXYGEN-CONTAINING ADDITIVE AS AN ECOLOGICALLY BENEFICIAL COMPONENT FOR LIQUID MOTOR FUELS

PRIORITY CLAIM

This application is a continuation of International Application PCT/IB2007/004121, which was filed on Dec. 27, 2007, now abandoned, which claims the benefit of the filing date of Ukrainian Application No. 200704667, which was filed on Apr. 26, 2007.

BACKGROUND OF THE INVENTION

The present invention generally relates to devices for producing oxygen-containing substances from hydrocarbon, and, more particularly, the present invention relates to devices for implementing a process for producing oxygen-containing additives (OCA) for all of the liquid motor fuels and may be practiced in various industries of economy where, for example, internal combustion engines are used.

Widely known in science and technology are processes for producing a wide range of organic oxygen-containing substances from hydrocarbon, which contains oxygen bound to the carbon skeleton of a compound, the atoms whereof are included in hydroxyl (carbonyl, carboxyl) groups and determine the chemical properties of compounds. Adding oxygen-containing substances from hydrocarbon, in appropriate proportions, to all liquid motor fuels, improves liquid motor fuels combustion efficiency, and thereby reduces emission of harmful substances to the atmosphere.

Therefore, what is needed is the development of devices for implementing a process for producing an oxygen-containing additive for all of the liquid motor fuels, which have high chemical and physical stability, and the components of which are not deficient and are readily available.

Known in the science is a plant for producing the oxygen-containing additive for gasoline, which comprises a fermentation cylinder, a dehydration cylinder, a recovery cylinder, and heat exchange and auxiliary equipment. The oxygen-containing additive produced at this plant comprises dehydrated ethanol and, after mixing with gasoline, is hygroscopic and, is not stable for storage upon moisture, as well as at low temperatures. Therefore, blends of OCA's with gasoline do not ensure stability for motor fuel properties during long-term storage, particularly at higher humidity and low temperatures.

The physical stability of motor fuel compositions is ensured by adding, in appropriate proportions, stabilizers and additives, which improve motor fuels functional properties, such as wash and antiknock agents. Such additives, as well as compositions containing them, are prepared by means of ordinary mixing, using standard equipment. It should be pointed out that the presence of a great amount of stabilizers in such additives and the addition of such additives to a fuel composition, result in increased costs, while the presence of gasoline-based components produced by the oil-refining industry in fuel compositions, results in rising prices and scarcities, for example, because of the Ukraine's energy dependence on imported energy.

The most similar in the technological spirit to the plant in accordance with this invention is, chosen as a prototype, a biogas plant for processing and recycling agriculture organic waste, which comprises a mixing tank, an anaerobic fermentation vessel of liquid biomass, a gasholder, a system for removal of sulphuretted hydrogen and a hotwell. This known plant implements a method for producing oxygen-containing substances from hydrocarbon by means of the anaerobic decomposition of a liquid biomass based on the bio-chemical degradation (fermentation hydrolysis) of organic substances and receiving the production of a colloidal solution of organic oxygen-bearing compounds, such as volatile fatty acids, alcohols, aldehydes, and ketones; and concomitant gases, such as carbon-dioxide gas, hydrogen, sulphuretted hydrogen, methane, ammonia; and inorganic substances, such as Ca, Co, Cu, K, Mg, Mn, Mo, N, P, S, Zn.

The principal disadvantage of the prototype is that this known biogas plant is incapable of producing the oxygen-containing additive for liquid motor fuels in the form of an environment-friendly, phase-stable colloidal composition of organic and inorganic substances because of the instability of its oxygen-bearing components.

Accordingly, an object of the present invention is to provide a plant for producing an OCA as an ecologically beneficial component for liquid motor fuels by equipping the known biogas plant with additional devices and by introducing a new interrelationship between the structural components of the plant.

The technical result achieved by implementing of this invention is the improvement of both chemical and physical stability of the performance indices of the oxygen-bearing components of a colloidal substance.

As a result, consumer properties of the subject-matter of the invention are connected with the technical result, i.e., the implementation of a technology of producing an OCA as an ecologically beneficial component for liquid motor fuels to ensure the stability of composition fuel properties during long-term storage.

The technical result is achieved by the known biogas plant comprising the mixing tank, the anaerobic fermentation vessel of liquid biomass, the gasholder, the system for removal of sulphuretted hydrogen, and the hotwell, and further comprising an aerobic fermentation vessel provided with stop and control valves, a device for pumping of liquid substance after fermentation, a device for liquid aeration with an oxygen-containing gas, and a removal system of solid mass residue after fermentation; a gas distribution device; a device for utilization of heavy gases; a device for ammonia adsorption by water; a liquid-gas mixer; a cavity mixer; a system that serves superficial active and dispersant matters and a cooler; all of these being connected to each other by pipelines. A bottom of the gas distribution device is connected by pipelines to the aerobic fermentation vessel and to the device for utilization of heavy gases, and a top of the gas distribution device is connected to the cavity mixer through the device for ammonia adsorption by water and through the liquid-gas mixer.

The above listed features, which are distinctive from those of the prototype, constitute the spirit of the invention and are novel, since they are necessary and sufficient for attaining the set object, i.e., to provide a plant for producing an OCA as an ecologically beneficial component for liquid motor fuels.

The comparison of the solution in accordance with the present invention with other prior technical solutions shows that the features of the solution in accordance with the present invention, namely: the devices connected to each other by pipelines from the list of which is given above and which complement the known biogas plant have not been detected in the known plants for producing an OCA for liquid motor fuels.

In order to demonstrate the cause-and-effect relationship between the aggregate of the dominant features of the device in accordance with the present invention and the technical results, the applicant submits as follows:

As a result of complementing the biogas plant with the aerobic fermentation vessel, aerobical satiation of fermented liquid substance by an oxygen-bearing gas is discovered:

The cessation of any further anaerobic decomposition of the liquid biomass;

Increase in the number of free radicals and hydroxyl groups;

Further oxidation accompanied by the production of complex blends with an oxygen-containing compounds; and The improvement of ergonomic characteristics due to the elimination of an unpleasant odor.

The gases produced during the aerobic fermentation of the liquid substance are accumulated in the gas distribution device and are distributed within it vertically depending on their molecular weights. This allows utilization of sulphuretted hydrogen by passing it through the device for utilization of heavy gases, as well as ammonia with water as a fertilizer to be produced by passing the mixture of light gases ($H_2$, $CH_4$, $NH_3$) through the device for ammonia adsorption by water.

The employment, in the biogas plant in accordance with the present invention, of the cavity mixer and of the system that serves superficial active and dispersant matters to the liquid substance after saturation aerobically by oxygen-containing gases, enables this substance to be stabilized, due to the cessation of chain reactions. In addition, the performance indices of its oxygen-bearing components are improved. The use of a vibrating device in the cavity mixer allows the colloidal substance to be activated by an ultrasonic frequency of vibrations with predetermined parameters; this results in:

The final destruction of anaerobic and aerobic bacteria cells;

An additional to formation of emulsion;

Solid particle dispersion to a size of near $10^{-7}$ m;

Change in the confirmational structure of molecules, in spatial orientation and properties, and in chain deformation and fragmentation;

The production of free, highly active radicals (CH), ions ($OH^-$ and $H^+$), lower molecular weight hydrocarbons, molecular hydrogen, and atomic oxygen.

Therefore, the employment, in the biogas plant in accordance with the present invention, of the cavity mixer and of the system that serves superficial active and dispersant matters provides that the aggregate transformations and physical stability of the performance indices of the oxygen-containing components of the colloidal substance are ensured. This in turn allows long-term storage of a mixture of liquid motor fuels with an OCA to be achieved.

Equipping the biogas plant, in accordance with the present invention, with the cooler (heat exchanger—distiller) makes it possible to condense the gases produced during the process of activating the colloidal mass by ultrasonic cavitation and to provide a plant for producing the oxygen-containing additive as an ecologically beneficial component for liquid motor fuels in the form of a high dispersion, physically stable colloidal substance.

BRIEF DESCRIPTION OF THE DRAWING

FIG. 1 is a schematic diagram of the plant for producing an OCA as an ecologically beneficial component for liquid motor fuels, in accordance with the present invention.

DETAILED DESCRIPTION OF THE INVENTION

The plant in accordance with the present invention comprises a mixing tank 1, an anaerobic fermentation vessel of liquid biomass 2, a gasholder 3, an aerobic fermentation vessel 4, a device for pumping of liquid substance after fermentation 5, a device for liquid aeration 6, a removal system of solid mass residue after fermentation 7, a gas distribution device 8, a device for utilization of heavy gases 9, a device for ammonia adsorption by water 10, a liquid-gas mixer 11, a system that serves superficial active and dispersant matters 12, a cavity mixer 13, a cooler (heat exchanger—distiller) 14, a hotwell 15, and a system for removal of sulphuretted hydrogen 16; all of these being connected to each other by pipelines.

A bottom of the gas distribution device 8 is connected by pipelines to the aerobic fermentation vessel 4 and to the device for utilization of heavy gases 9, and a top of the gas distribution device 8 is connected to the cavity mixer 13 through the device for ammonia adsorption by water 10 and through the liquid-gas mixer 11.

The operation of the plant in accordance with the present invention will now be described in detail:

A liquid substance containing an agricultural organic waste is fed from the mixing tank 1 to the anaerobic fermentation vessel 2 where the process of anaerobic decomposition of the liquid biomass and of the production of a colloidal solution of organic and inorganic substances takes place. The gases produced during the anaerobic decomposition of the liquid matter are accumulated in the gasholder 3 and pass to a consumer through the system for removal of sulphuretted hydrogen 16.

The colloidal substance is pumped from the anaerobic fermentation vessel 2 by a pump of the device for pumping of liquid substance after fermentation 5 to the aerobic fermentation vessel 4 and is saturated with an oxygen-bearing gas by means of nozzles of the liquid aeration device 6.

Under blend pressure, gases are produced during the liquid substance fermentation process within the aerobic fermentation vessel 4, the liquid substance saturated with the oxygen-containing gas enters the cavity mixer 13 within which it is mixed with superficial-active and dispersive action salts of alkali metals, added thereto, in a predetermined proportion by the system that serves superficial active and dispersant matters 12. The gases from the aerobic fermentation vessel 4 accumulated in the gas distribution device 8 are distributed within it vertically depending on their molecular weights. Heavy gases go to the device for utilization of heavy gases 9, while light gases enter the cavity mixer 13 through the device for ammonia adsorption by water 10 and through the liquid-gas mixer 11.

The liquid substance formed after mixing within the cavity mixer 13 is fed to a mechanical activator of the cavity mixer 13 and then the liquid is activated by ultrasonic cavitation with predetermined parameters on ultrasonic frequency of vibrations. Gases are produced upon liquid activation by ultrasonic cavitation, the temperature whereof achieves between near 55° C. to 105° C. The contents having passed through the cooler 14 and the produced liquid substance in the form of an environment-friendly oxygen-containing additive enter the hotwell 15. The solid phase of the liquid substance from the anaerobic fermentation vessel 2 and from the aerobic fermentation vessel 4 is directed as a fertilizer to a consumer through the removal system of solid mass residue after fermentation 7.

The plant in accordance with the present invention implements the process for producing oxygen-containing additive from hydrocarbon, which makes it possible to:

Produce an inexpensive oxygen-containing additive as an ecologically beneficial component for all of the liquid motor fuels from a liquid colloidal phase of the decomposition of the biological waste of farm animals;

Produce an inexpensive oxygen-containing additive as an ecologically beneficial component for all of the liquid motor fuels from the biological waste of vegetable biomass;

Produce an inexpensive oxygen-containing additive as an ecologically beneficial component for all of the liquid motor fuels from the biological waste of farm animals and of vegetable biomass;

Produce an inexpensive oxygen-containing additive as an ecologically beneficial component for all of the liquid motor fuels from a liquid colloidal phase of the decomposition of the biological waste of people biomass;

Produce an inexpensive oxygen-containing additive as an ecologically beneficial component for all of the liquid motor fuels from a liquid colloidal phase of the decomposition of the biological waste of farm animals and of people biomass;

Produce an inexpensive oxygen-containing additive as an ecologically beneficial component for all of the liquid motor fuels from a liquid colloidal phase of the decomposition of the biological waste of vegetable biomass and of people biomass;

Produce an inexpensive oxygen-containing additive as an ecologically beneficial component for all of the liquid motor fuels from a liquid colloidal phase of the decomposition of the biological waste of farm animals, of vegetable biomass, and of people biomass;

Use the solid phase of the decomposition of the biological waste of farm animals, of vegetable biomass and of people biomass as fertilizers; and Improve the environmental situation in Ukraine and other countries.

The plant in accordance with the present invention has passed tests successfully at one of the leading companies of the agro-industrial complex of Ukraine Agro-Soyuz. The tests performed involving a mixture of an oxygen-containing additive with diesel fuel has revealed substantial advantages of this fuel mixture over pure fuel, namely:

The consumption of diesel fuel in its mixture with an OCA decreases by nearly 22%;

Complete absence of the coking of the fuel equipment elements, of carbon deposit and luster on the piston group elements in an internal combustion engine;

Emissions of harmful substances are reduced substantially;

The fuel mixture has stable physical properties; and

The assessed value of cost of the fuel blend with an OCA added is lower by nearly 15% than that of pure fuel.

The production of an OCA for liquid motor fuels at the plant in accordance with the present invention, the use of the solid phase of the decomposition of the biological waste of farm animals and of vegetable biomass as fertilizers, and environmental improvements due to recycling agricultural organic waste and of people biomass ensure wide opportunities of using the plant in accordance with the present invention in various industries of economy.

The invention claimed is:

1. A plant for producing oxygen-containing additives as ecologically beneficial components for liquid motor fuels, the plant comprising:

a mixing tank containing a liquid biomass;

an anaerobic fermentation vessel that receives from the mixing tank the liquid biomass in which anaerobic decomposition of the liquid biomass and production of a colloidal solution of organic and inorganic substances occur;

a gasholder that receives from the anaerobic fermentation vessel any gases produced through the anaerobic decomposition of the liquid biomass;

a system for removal of sulphuretted hydrogen that receives the gases from the gasholder and removes sulphuretted hydrogen from the gases;

a pumping device that pumps the colloidal solution produced in the anaerobic fermentation vessel;

an aerobic fermentation vessel provided with stop and control valves that receives the colloidal solution from the anaerobic fermentation vessel through the pumping device in which gases are produced during a fermentation process of the colloidal solution, the aerobic fermentation vessel comprising a device for liquid aeration with an oxygen-containing gas that saturates the colloidal solution with the oxygen-containing gas;

a cavity mixer that receives from the aerobic fermentation vessel any liquid phase of the saturated colloidal solution;

a removal system of solid mass residue that receives from the aerobic fermentation vessel any solid phase of the colloidal solution;

a gas distribution device that receives from the aerobic fermentation vessel any gas phase of the colloidal solution, wherein the gas phase comprises heavy and light gases that are distributed vertically within the as distribution device depending on their molecular weights;

a device for heavy gases utilization that is connected to a bottom portion of the gas distribution device and receives the heavy gases, which are distributed toward the bottom of the gas distribution device;

a device for ammonia adsorption by water that is connected to a top portion of the gas distribution device and receives the light gases, which are distributed toward the top of the gas distribution device, in which a liquid substance is produced;

a liquid-gas mixer that receives from the device for ammonia adsorption by water the produced liquid substance and the light gases in which the produced liquid substance and the light gases are intermixed, wherein the liquid-gas mixer is connected to the cavity mixer so that the cavity mixer receives the intermixed liquid substance;

a system that serves superficial active and dispersant matters for adding into the cavity mixer a predetermined amount of superficial active and dispersant matters, wherein the cavity mixer mixes any liquid that it receives and the superficial active and dispersant matters and then activates the mixed liquid by ultrasonic cavitation upon which gases are produced;

a cooler that receives the gases from the cavity mixer in which an oxygen-containing liquid is produced; and a hotwell that receives the oxygen-containing liquid from the cooler.

2. The plant as claimed in claim 1, characterized in that a gas pipeline connecting the top portion of the gas distribution device to the liquid-gas mixer has the capability of evacuating ammonia from the light gases in the device for ammonia adsorption by water and not enabling ammonia outlet to the liquid-gas mixer.

3. The plant as claimed in claim 1, wherein the liquid biomass comprises biological waste of farm animals.

4. The plant as claimed in claim 1, wherein the liquid biomass comprises biological waste of vegetable biomass.

5. The plant as claimed in claim 1, wherein the liquid biomass comprises biological waste of people biomass.

6. The plant as claimed in claim 1, wherein the liquid biomass comprises at least two of: biological waste of farm animals, biological waste of vegetable biomass, and biological waste of people biomass.

7. The plant as claimed in claim 1, wherein the solid phase of the colloidal solution is used as a fertilizer.

8. The plant as claimed in claim 1, wherein the heavy gases comprise sulphuretted hydrogen.

9. The plant as claimed in claim 1, wherein the light gases comprise $H_2$, $CH_4$, and $NH_3$.

10. The plant as claimed in claim 1, wherein the superficial active and dispersant matters comprise salts of alkali metals.

11. The plant as claimed in claim 1, wherein the temperature of the gases produced upon ultrasonic cavitation ranges between about 55° C. to about 105° C.

* * * * *